(12) United States Patent
Hegenberger

(10) Patent No.: US 12,290,246 B2
(45) Date of Patent: May 6, 2025

(54) VAGINAL SPECULUM

(71) Applicant: HEGENBERGERSPECULUM APS, Karrebæksminde (DK)

(72) Inventor: Malene Hegenberger, Karrebæksminde (DK)

(73) Assignee: HEGENBERGERSPECULUM APS, Karrebæksminde (DK)

( * ) Notice: Subject to any disclaimer, the term of this patent is extended or adjusted under 35 U.S.C. 154(b) by 591 days.

(21) Appl. No.: 17/608,219

(22) PCT Filed: May 7, 2020

(86) PCT No.: PCT/EP2020/062707
§ 371 (c)(1),
(2) Date: Nov. 2, 2021

(87) PCT Pub. No.: WO2020/225360
PCT Pub. Date: Nov. 12, 2020

(65) Prior Publication Data
US 2022/0273168 A1 Sep. 1, 2022

(30) Foreign Application Priority Data
May 9, 2019 (GB) ..................... 1906562

(51) Int. Cl.
*A61B 1/00* (2006.01)
*A61B 1/303* (2006.01)
(Continued)

(52) U.S. Cl.
CPC .......... *A61B 1/303* (2013.01); *A61B 1/00142* (2013.01); *A61B 1/00148* (2022.02); *A61B 1/32* (2013.01); *A61B 17/42* (2013.01)

(58) Field of Classification Search
CPC .......... A61B 1/303; A61B 1/32; A61B 17/42; A61B 1/00148; A61B 1/00142
See application file for complete search history.

(56) References Cited

U.S. PATENT DOCUMENTS 3,030,947 A 4/1962 Engelbert
4,632,093 A 12/1986 Giorni
(Continued)

FOREIGN PATENT DOCUMENTS

AU 2004100346 6/2004
CN 201337440 Y 11/2009
(Continued)

OTHER PUBLICATIONS

International Search Report and Written Opinion were mailed on Jan. 28, 2019 by the International Searching Authority for International Application No. PCT/EP2018/080842 filed on Nov. 9, 2018 and published as WO 2019/092222 (Applicant—Hegenbergerspeculum APS) (13 pages).

(Continued)

*Primary Examiner* — Eduardo C Robert
*Assistant Examiner* — Holly Joanna Lane
(74) *Attorney, Agent, or Firm* — Ballard Spahr LLP

(57) ABSTRACT

Described is a vaginal speculum having a vaginal assembly of at least two longitudinal elements connected at a distal end for insertion into the vagina of a subject. The vaginal speculum is configured for holding the vaginal walls of the subject apart, thereby permitting examination and/or suturing of at least the posterior part of the vaginal tissue.

19 Claims, 5 Drawing Sheets

(51) Int. Cl.
*A61B 1/32* (2006.01)
*A61B 17/42* (2006.01)

(56) References Cited

U.S. PATENT DOCUMENTS

| | | | |
|---|---|---|---|
| 4,966,130 A | 10/1990 | Montaldi | |
| 5,018,507 A | 5/1991 | Montaldi et al. | |
| 6,312,377 B1* | 11/2001 | Segermark | A61B 17/02 |
| | | | 600/210 |
| 7,607,917 B2 | 10/2009 | Virnicchi et al. | |
| 2006/0135853 A1 | 6/2006 | Chin | |
| 2008/0114210 A1* | 5/2008 | Shah | A61B 1/32 |
| | | | 264/80 |
| 2009/0081611 A1 | 3/2009 | Hines et al. | |
| 2010/0041954 A1* | 2/2010 | Bastia | A61B 1/32 |
| | | | 600/210 |
| 2011/0034776 A1* | 2/2011 | Dixon | A61B 1/32 |
| | | | 600/235 |
| 2013/0053863 A1 | 2/2013 | Juravic et al. | |
| 2013/0253376 A1 | 9/2013 | Juravic et al. | |
| 2014/0303447 A1 | 10/2014 | Singh et al. | |
| 2015/0045485 A1 | 2/2015 | Tsutimoto et al. | |
| 2017/0181607 A1 | 6/2017 | Lalli et al. | |
| 2018/0014721 A1 | 1/2018 | Rullo et al. | |
| 2018/0344144 A1 | 12/2018 | Bouquet | |
| 2019/0000353 A1 | 1/2019 | Carty | |
| 2019/0167464 A1 | 6/2019 | Lovato et al. | |
| 2019/0350670 A1* | 11/2019 | Grey | A61B 17/02 |
| 2020/0060517 A1* | 2/2020 | Roychowdhury | A61B 1/00101 |

FOREIGN PATENT DOCUMENTS

| | | |
|---|---|---|
| CN | 101889856 | 11/2010 |
| GB | 1462929 | 1/1977 |
| GB | 1462929 A | 1/1977 |
| GB | 2275421 A | 8/1994 |
| JP | 2003062081 A | 3/2003 |
| WO | WO 96/12437 A1 | 5/1996 |
| WO | WO 2015/031282 | 3/2015 |
| WO | WO 2019/092222 A1 | 5/2019 |

OTHER PUBLICATIONS

International Search Report and Written Opinion for PCT/EP2020/062707, filed May 7, 2020, and Published as WO 2020/225360 on Nov. 12, 2020 (11 pages).

* cited by examiner

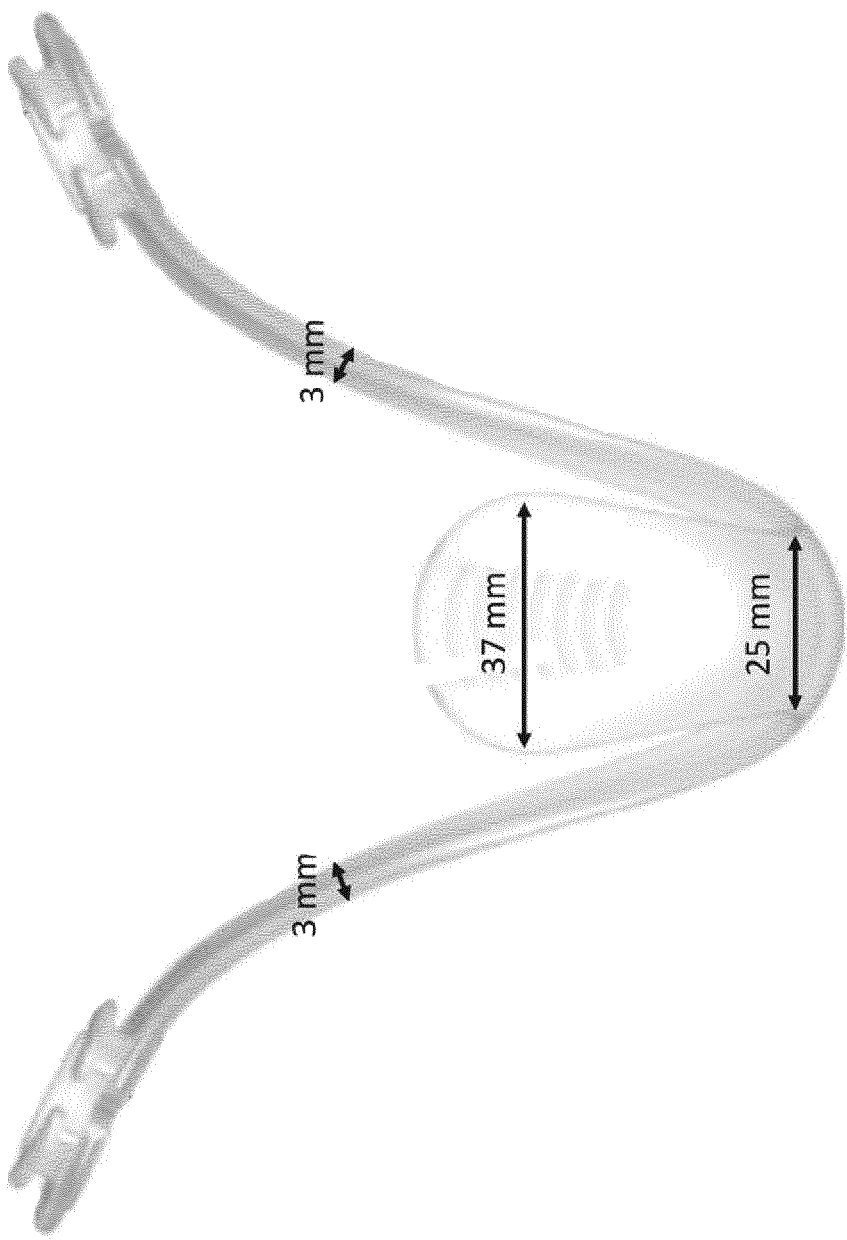

VAGINAL SPECULUM

CROSS-REFERENCE TO RELATED APPLICATIONS

This application is a U.S. National Phase Application of International Application No. PCT/EP2020/062707, filed May 7, 2020, which claims priority to Great Britain Patent Application No. 1906562.2, filed May 9, 2019, each of which are hereby incorporated by reference in their entirety.

FIELD OF INVENTION

The present invention relates to a vaginal speculum configured to permit an unobstructed view of at least the posterior part of the vaginal tissue during, examination and/or suturing of the vaginal tissues.

The vaginal speculum of the invention is of a design that is ergonomic for the patient and the user, providing an unobstructed view of the vaginal tissue and access for examination, suturing, surgery or training purposes.

BACKGROUND OF INVENTION

An instrument known as a speculum is a commonly-used medical tool for opening and/or distending an orifice and/or cavity of a patient to permit examination of the interior and/or to enable a sample to be taken, and/or for operation. Various forms of specula are known, their designs varying in accordance with the body cavity to be inspected (e.g. vagina, rectum, ear, nostril).

Specula for vaginal examination purposes typically comprise one or, more commonly, two blades which are used to move the vaginal walls into position when an operator is carrying out examinations/surgery.

One-bladed specula consist of a single blade. One-bladed specula allow for more exposure of vaginal walls by sliding down or around the surface of the vaginal walls and do not restrict the exposure and are thus useful in surgery. However, these specula need an assistant for adequate exposure and also need anterior wall retractors to expose the cervix.

Two-bladed specula or bivalved specula consists of two blades. Bivalved specula are generally used in outpatient departments for examination of vagina and cervix. They can also be used for minor procedures like intrauterine device (IUD) insertion or cauterization of cervical erosion, colposcopy and the like.

Currently used vaginal specula contain two blades as outlined above which are connected towards their proximal end via a traction mechanism, which is typically in the form of an external lever and screw mechanism, which when actuated, forces the two blades apart so as; to dilate the vaginal walls. The external lever and screw mechanism also act as a locking mechanism so that the blades remain at a set distance when in use.

However, not only are such devices uncomfortable for the patient, but they also highly restrict the view of, and accessibility to, the vaginal cavity by the operator, which can lead to serious complications such as vaginal tears not being fully sutured after a patient has given birth leading to the patient requiring resuturing, or worse, infections setting in.

Where the use of a speculum as described above is not practicable, due to the restricted access such specula result in, the operator will instead use the fingers of one or both hands to dilate the vagina for examination and then hold one or more fingers of one hand in place as a guide for suturing while unable to see the actual suturing location. The fingers of one or both hands are then used again to dilate the vagina to inspect the suturing result. When training students, the trainer may use their fingers to dilate the vagina while the student performs suturing, requiring both student and trainer to assume constrained postures for extended periods. Furthermore, since the operator is unable to see inside the vaginal cavity in such situations, there is a high risk of needle stick injury to the operator(s) which can lead to cross-contamination between the patient and operator.

This use of potentially painful or damaging hooks or traction devices, poor or no visibility of the operating area, and constrained postures and hand positions often result in a protracted and difficult procedure for both the patient and the operator or student and trainer. This has a corresponding effect on the suturing results, sometimes necessitating resuturing and the constrained positions can lead to infections setting in and/or cross-contamination from needle-stick injuries.

Due to the abovementioned difficulties associated with examination or operation of the vagina, it is an object of the present invention to provide an improved vaginal speculum that provides a clearer, less obstructed view of the area to be examined, sutured or operated on that facilitates the suturing process, and which is furthermore easier to handle. The most common area of vaginal tearing that occurs during childbirth is in the vaginal floor, being the lateral wall of the vagina and the perineum (the area between the vagina and the anus— including the anal sphincter muscle) also referred to herein as the posterior vaginal wall. Many specula have their handles or locking mechanisms in this location, obstructing the view.

Specifically, it is an object of the present invention to provide a vaginal speculum that facilitates examination or operation without the additional use of hooks or of the fingers of the operator or trainer, and which is able to be retained within the vagina without the use of an actuation/locking mechanism at the proximal end of the device.

According to the present invention, there is provided a vaginal speculum comprising:
  a vaginal assembly comprising two longitudinal elements each having a proximal and distal end and being connected towards their distal ends, wherein each longitudinal element comprises an inner and an outer surface;
  wherein the vaginal speculum is configured for holding the vaginal walls of the subject apart via the longitudinal elements, wherein the outer surfaces of the longitudinal elements are configured to be in contact with the vaginal walls of the subject whilst in use and wherein the vaginal assembly is fabricated at least partially from an elastic material having a flexural modulus of from about 1000 MPa to about 3500 MPa.

According to another aspect of the present invention, there is provided a vaginal speculum comprising:
  a vaginal assembly comprising two longitudinal elements each having a proximal and distal end and being connected towards their distal ends, wherein each longitudinal element comprises an inner and an outer surface;
  wherein the vaginal speculum is configured for holding the vaginal walls of the subject apart via the longitudinal elements, wherein the outer surfaces of the longitudinal elements are configured to be in contact with the vaginal walls of the subject whilst in use and at least a portion of one or both the outer walls has a surface roughness of from about 5 to about 31 micrometers Ra.

According to another aspect of the invention, there is provided an array of vaginal specula comprising a plurality of specula as defined above, wherein each speculum in the set differs in at least one dimension to each other speculum so as to provide a range sizes of specula to fit different subject anatomies.

According to a further aspect of the invention, there is provided a sterile, hermetically sealed container, comprising a vaginal speculum as defined above, or an array of vaginal specula as defined above for single use.

According to another aspect of the invention, there is provided a method for inserting a vaginal speculum into the vagina of a subject, wherein the method comprises the steps of providing a vaginal speculum as defined above and inserting the distal end of the speculum into the vagina of the subject.

According to a further aspect of the invention, there is provided a method of use of the vaginal speculum as defined above during vaginal suturing after the subject has given birth.

According to another aspect of the invention, there is provided a method of providing, an unobstructed view of at least the posterior part of the vaginal wall during examination of a subject after said subject has given birth comprising the step of
  inserting a vaginal speculum as defined above into the vagina of a subject using the method as defined above.

According to a further aspect of the invention, there is provided a method of suturing vaginal tissue comprising the steps of:
  inserting a vaginal speculum as defined above into the vagina of a subject using the method as defined above; and
  suturing a tear in the vaginal tissue of the subject.

According to another aspect of the invention, there is provided a vaginal speculum comprising:
  a vaginal assembly comprising two longitudinal elements each having a proximal and distal end and being connected towards their distal ends, wherein each longitudinal element comprises an inner and an outer surface;
    wherein the vaginal speculum is configured for holding the vaginal walls of the subject apart via the longitudinal elements, wherein the outer surfaces of the longitudinal elements are configured to be in contact with the vaginal walls of the subject whilst in use and at least a portion of one or both the outer walls comprise high impact polystyrene.

Definitions

Anterior vaginal wall: front wall, of the vagina, behind which is located the bladder and urethra of the subject.

Posterior vaginal all: rearward wall of the vagina, behind which is located the rectum and anus.

Lateral vaginal walls: vaginal walls connecting the anterior and posterior walls of the vagina on each side.

Distal end: defines the end of the vaginal speculum furthest away from the medical practitioner when in use. In other words, it is the end of the speculum which is first inserted into the vagina of the subject when in use.

Proximal end: the proximal end defines a part of the speculum which is closest to the medical practitioner when in use.

Inner surface: refers to the part of the surface of speculum assembly facing away from the vaginal wall it is closest to when inserted into the vagina.

Outer surface: refers to the part of the surface of the speculum facing toward the vaginal walls and/or configured to be in contact with the vaginal wall it is closest to after the speculum is inserted into the vagina.

Ra: is calculated by an algorithm that measures the average length between the peaks and valleys and the deviation from the mean line on the entire surface within the sampling length. Ra averages all peaks and valleys of the roughness profile and then neutralizes the few outlying points so that the extreme points have no significant impact on the final results. The Ra value is preferably measured according to ISO 4827.

Herein, elastic material is understood as being a material that is capable of returning to its original length, shape or configuration after being deformed, where deformation may refer to stretching, compression or expansion. An elastic material may be able to return or recover its original shape and size spontaneously after deformation. Elastic may further refer to materials exerting a force on its surroundings when deformed, as the material seeks to return to its original shape. Elastic materials may be, for example, formed of a rubber, polymer or metal.

DESCRIPTION OF DRAWINGS

The embodiments of the invention, together with its advantages, may be best understood from the following detailed description taken in conjunction with the accompanying figures.

FIG. 5 corresponds to FIG. 3 and has been annotated to show the dimensions of this device.

DETAILED DESCRIPTION OF THE INVENTION

Figure 1:
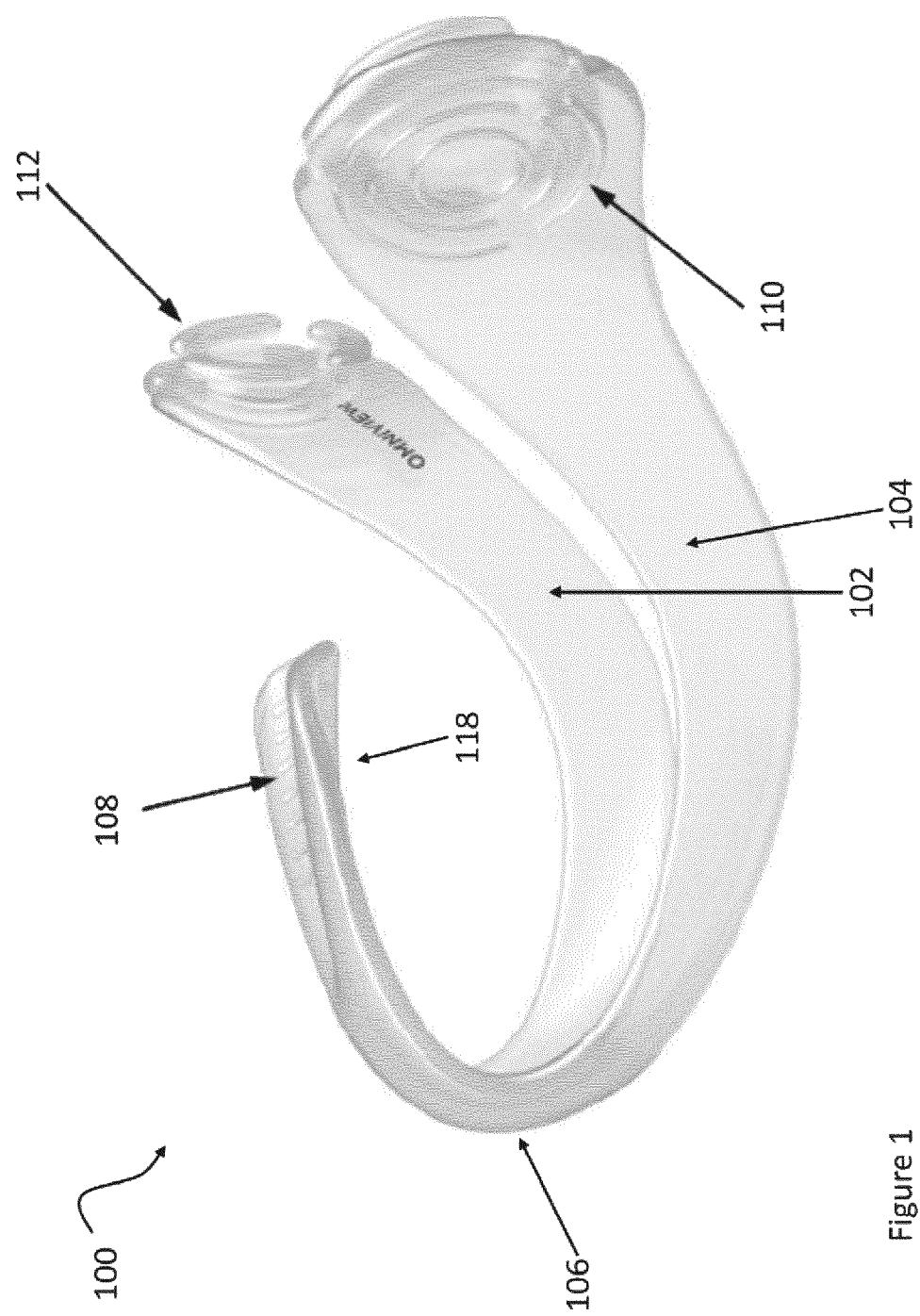
FIG. 1 is a side view of a vaginal assembly according to the present invention.

According to the invention, a vaginal speculum comprising a vaginal assembly comprising two longitudinal elements is disclosed. The two longitudinal elements each have a proximal end and a distal end and are connected towards their distal ends. The vaginal speculum is configured for holding the vaginal walls of a subject apart via the longitudinal elements. The longitudinal elements each have an inner and an outer surface, wherein at least part of the outer surface of one, or both of, the longitudinal elements are configured to be in contact with the vaginal walls of the subject whilst in use.

For the avoidance of doubt, any of the features described above or below are envisaged to be incorporated into the vaginal speculum defined in the preceding paragraph.

Known vaginal specula in the art often slip out of position after being inserted into the vagina of a subject. This may cause discomfort or pain for the subject. It may also prohibit examination and/or operation due to for example blocking of the practitioner's view. Re-positioning of the askew speculum may be necessary which is time-consuming and may require the assistance of a second practitioner such as a doctor, a nurse, a mid wife or a medical student.

The inventors have found that in order for the speculum to remain in place whilst in use without the need for additional locking mechanisms, the vaginal assembly should be made, at least partly, from an elastic material having a material has a flexural modulus of from about 1000 MPa to about 3500 MPa. The inventors have surprisingly found that providing an elastic material with a flexural modulus in this range provides the optimal level of pressure when the device is in place within the vagina of the subject to provide the force necessary for the device to remain in place.

Preferably, one or, both of the longitudinal elements comprise the elastic material having the flexural modulus described above. Conveniently, the longitudinal elements are predominantly composed of, or consist of, the elastic material having the flexural modulus as described above.

Conveniently, the vaginal speculum has a flexural modulus of from about 1500 MPa to about 3000 MPa, such as from about 1500 MPa to about 2750 MPa, for example from about 1500 MPa to about 2600 MPa, preferably from about 1900 MPa to about 2500 MPa.

Advantageously, the elastic material has a tensile modulus of from about 1000 MPa to about 3000 MPa, for example from about 1000 MPa to about 2900 MPa, such as from about 1000 MPa to about 2500 MPa, or from about 1500 MPa to about 2500 MPa preferably from about 1800 MPa to about 2200 MPa.

Conveniently, the elastic material may have a flexural strength of from about 10 MPa to about 100 MPa, such as from about 20 MPa to about 80 MPa, preferably from about 30 MPa to about 60 MPa, such as from about 35 to about 50 MPa.

Flexural properties such as flexural strength or flexural or bending modulus of elasticity may be measured using ASTM D790.

Conveniently, the elastic material may have a tensile strength of from about 5 MPa to about 40 MPa, such as from about 5 MPa to about 30 MPa, preferably from about 10 MPa to about 30 MPa, such as from about 15 to about 25 MPa.

Advantageously, the elastic material has a tensile elongation of from about 30 to about 70%, such as from about 40 to about 60 Vo.

Tensile properties such as tensile modulus or Young's modulus, tensile strength, or elongation may be measured according to ASTM D638.

Advantageously, the elastic material has a falling dart value of about 100 to about 150 kg-cm, such as about 110 to about 140 kg-cm, preferably about 120 to about 130 kg-cm. Preferably, the falling dart value is measured according to ASTM Test D-3029.

Conveniently, the vaginal speculum and/or the vaginal assembly is fabricated from a metal or polymeric material, preferably a polymeric material.

Conveniently, the vaginal speculum and/or the vaginal assembly is fabricated entirely from an elastic and/or resilient material.

Elastic materials are configured to return to their original length, shape or configuration after being deformed. Elastic materials may return or recover their original shape and size spontaneously after deformation.

Preferably, the polymeric material is selected from the group consisting of nylon, silicone, polyethylene (PE), polypropylene (PP), polystyrene (PS), high impact polystyrene (HIPS), polyvinyl chloride (PVC), polyester, polycarbonate, polysulfone, poly-p-xylylene, and mixtures thereof, preferably wherein the polymeric material is high impact polystyrene (HIPS).

High Impact Polystyrene (HIPS) has a Cas # of 9003-53-6 and is a form of polystyrene (PS) that carries with it a higher impact strength. Homopolymer PS can often be brittle and can be made more impact resistant if combined with other materials. This form of PS typically is produced by adding around 5-10% rubber or butadiene copolymer. This increases the toughness and impact strength, of the polymer.

Conveniently, the longitudinal elements may be connected at their distal end. Thus providing the assembly with a distal point. Preferably the longitudinal elements are concavely connected at their distal end, arriving at a rounded distal point on the vaginal assembly.

Advantageously, the longitudinal elements of the vaginal assembly are configured for holding the lateral vaginal walls of the subject apart.

Preferably, the longitudinal elements of the vaginal assembly have a maximum thickness of from about 0.1 to about 10 mm, for example about 0.5 to about 10 mm, such as about 1 to about 5 mm, preferably from about 2 to about 4 mm. Wherein, the thickness is defined as the distance from the outer, surface to the inner surface of the longitudinal elements.

Advantageously, the longitudinal elements of the vaginal assembly have a maximum width of from about 5 mm to about 40 mm, such as about 10 mm to about 30 mm, preferably from about 10 mm to about 25 mm. Wherein the width is defined as the length from one edge of the longitudinal element to the other edge. In other words, the width of the longitudinal elements is substantially orthogonal to the thickness vector.

Conveniently, the longitudinal elements have a maximum width at their mid-point of from about 5 mm to about 40 mm, such as about 10 mm to about 30 mm, preferably from about 10 mm to about 25 mm, most preferably from about 15 to 20 mm. The mid-point being the middle of the longitudinal elements measured from their furthest proximal point to the furthest distal point.

Conveniently, the vaginal speculum according to the present invention is configured to, return or recover its original shape and size spontaneously after deformation. Deformation may be caused by pressing the longitudinal elements toward each other. In particular, as described in more detail below, the longitudinal elements of the vaginal assembly may be configured to be resiliently compressible out of a first configuration into a second configuration and resiliently expandable to return toward the first configuration on ceasing compression. In such a configuration, the midsection and proximal ends of the longitudinal elements are compressed towards each other more than the distal ends, since the longitudinal elements are connected towards their distal ends.

The inventors have also found that the roughness of the outer surface of either of, or both of, the longitudinal elements can influence the retention of the speculum when in use, independently of the material used to fabricate the vaginal speculum and/or assembly.

Therefore, according to another aspect of the present invention, there is provided a vaginal speculum comprising:
    a vaginal assembly comprising two longitudinal elements each having a proximal and distal end and being connected towards their distal ends, wherein each longitudinal element comprises an inner and an outer surface;

wherein the vaginal speculum is configured for holding the vaginal walls of the subject apart via the longitudinal elements, wherein the outer surfaces of the longitudinal elements, are configured to be in contact with the vaginal walls of the subject whilst in use and wherein at least a portion of one or both the outer walls has a surface roughness of from about 5 to about 31 micrometers Ra.

For the avoidance of doubt, any of the features described above or below are envisaged to be incorporated into the vaginal speculum defined in the preceding paragraph.

Conveniently, the vaginal speculum and/or vaginal assembly has both the roughness on the outer surface of the longitudinal element(s) as defined above and is fabricated at least partially from the elastic material with a flexural modulus as defined above.

The outer surface(s) of the longitudinal elements having a roughness within the range of 5 to 31 micrometers Ra prevents the speculum from slipping out, of position once the speculum has been inserted and positioned in the vagina of the subject.

Preferably, the outer surfaces of the longitudinal elements configured to be in contact with the vaginal walls of the subject whilst in use have a surface roughness of from about 10 to about 26 micrometers Ra, preferably from about 14 to about 20 micrometers Ra, more preferably from about 16 to about 18 micrometers Ra, even more preferably about 18 micrometers Ra.

Advantageously, at least 50%© of one, or both, of the outer surfaces of the longitudinal elements configured to be in contact with the vaginal walls of the subject whilst in use has a roughness as defined above. For example, at least 60%, 70%, 80% or 90% of the outer surfaces of the longitudinal elements that are configured to be in contact with the vaginal wall of the subject whilst in use may have a surface roughness as outlined above.

Conveniently, the area of outer surface roughness may be continuous, that is to say that there are no substantial breaks in the roughness. Alternatively, the area of roughness may be discontinuous such that the areas of roughness may be interdispersed with smoother areas, which may be beneficial in manufacturing processes since as the surface roughness increases, the difficulty to remove the specula from the moulds increases. For example, the areas of roughness may be present in discrete bands which span the width of the longitudinal elements and are separated by smoother strips on the outer surface, or the areas of roughness may be present in alternative shapes on the surface.

Preferably, the outer surfaces of the portions of the longitudinal elements that are configured to be in contact with the vaginal walls when in use have a surface roughness according to Charmilles scale of roughness of from 40 to 50, such as from 40 to 45, as measured according to ISO 1302.

Conveniently, the edge (or rim) of the longitudinal elements and/or the anterior vaginal wall element (see below) is raised along the edge of the longitudinal elements configured to be within the vagina of the patient when in use. The edge may be raised by an amount of from 0.2 mm to 2 mm, such as from 0.5 to 1.5 mm, preferably from about 0.8 to about 1.2 mm from the thickness of the main body of the longitudinal elements.

The raised edge provides added strength to the vaginal speculum/assembly when in use and also serves as a depth limitation indication to guide the operator as, to how far the vaginal assembly has been inserted into the subject's vagina.

According to another aspect of the invention, there is provided a vaginal speculum comprising:

a vaginal assembly comprising two longitudinal elements each having a proximal and distal end and being connected towards their distal ends, wherein each longitudinal element comprises an inner and an outer surface;
wherein the vaginal speculum is configured for holding the vaginal walls of the subject apart via the longitudinal, elements, wherein the outer surfaces of the longitudinal elements are configured to be in contact with the vaginal walls of the subject whilst in use and at least a portion of one or both the outer walls comprise high impact polystyrene.

For the avoidance of doubt, any of the features described above or below are envisaged to be incorporated into the vaginal speculum defined in the preceding paragraph.

Preferably, substantially all of the longitudinal elements are fabricated from high impact polystyrene. Advantageously, substantially all of the vaginal assembly and/or the vaginal speculum is fabricated from high impact polystyrene.

Advantageously, the polymeric material is of medical grade and of clear transparency enabling maximum visibility for gynaecological procedures such as cervical smear tests, IUD fittings, suturing after giving birth, and the like.

Conveniently, the proximal ends of the longitudinal elements are configured to, remain outside of the vaginal cavity when in use. This allows for the operator to easily compress the longitudinal elements together and remove the vaginal speculum once finished with.

The vaginal assembly may further comprise proximal base elements located at the proximal end of the longitudinal elements, wherein the proximal base elements are configured to rest on the skin outside the vagina after the vaginal assembly has been inserted into the vagina. One purpose of the base elements is that they may provide better comfort for the subject when the vaginal speculum is inserted into the vagina and to provide better protection of the sensitive tissue of the subject when in contact with the vaginal speculum. The proximal base elements may be flattened and/or curve outwards from the separating elements such that they can rest on the skin outside the vagina after the vaginal assembly has been inserted into the vagina. Alternatively, the proximal base elements are flattened and extending transversely such that they can rest on the skin outside the vagina, after the vaginal assembly has been inserted into the vagina. The proximal base elements are preferably located at the proximal ends of the separating elements. Furthermore, the proximal base elements are preferably configured for resting against, separating and holding apart the labia majora and labia minora.

Advantageously, the vaginal assembly further comprises an anterior vaginal wall element configured for supporting the anterior vaginal wall. Preferably, wherein the anterior vaginal wall element comprises a distal end and a proximal end.

Conveniently, anterior vaginal wall element is connected at the distal end of the vaginal assembly with the distal ends of the longitudinal elements, wherein the anterior vaginal wall element extends in the proximal direction from the distal end.

Preferably, the anterior vaginal wall element is in the shape of a tongue such as a flattened and rounded shape.

Advantageously, the vaginal assembly is configured for supporting the anterior vaginal wall after insertion into the vagina.

Conveniently, the vaginal assembly is configured for supporting the anterior vaginal wall after insertion into the vagina via the anterior vaginal wall element. The anterior vaginal wall element may thereby at least temporarily deform when inserted into the vagina such that it exerts a force on the anterior vaginal wall of the subject. Preferably, the vaginal assembly is configured for supporting the pressure exerted by the bladder on the anterior vaginal wall of the subject. This configuration of the speculum comprising an anterior vaginal wall element has a particular advantage in providing a clearer and less obstructed view of the posterior section of the vagina, in particular the perineum, which is where the majority of tearing occurs during child birth.

Preferably, the anterior vaginal wall element comprises an inner and an outer surface, wherein at least part of the outer surface is configured to be in contact with the anterior vaginal wall of the subject when in use.

Advantageously, the part of the outer surface of the anterior vaginal wall element that is configured to be in contact with the vaginal wall of the subject when in use is configured as detailed above with regard to the surface properties of the longitudinal elements. That is to say, for example, that the part of the outer surface of the anterior vaginal wall element configured to be in contact with the anterior vaginal wall in use may have an Ra value as described above.

Conveniently, the anterior vaginal wall element is fabricated from an elastic material as described above and may have any of the properties of the elastic material as described herein.

Preferably, the anterior vaginal wall element comprises a surface profile, on the outer surface, that is adapted to be grasped by the user on insertion and removal. Advantageously, the surface profile is located at or towards the proximal end of the anterior vaginal wall element and is in the form of raised ridges or bumps, such as hemispherical bumps. Preferably, the surface profile adapted to be grasped by the user is located in a depressed region at or towards the proximal end of the anterior vaginal wall element.

Advantageously, the anterior vaginal wall element has a maximum thickness corresponding to the maximum thickness of the longitudinal elements as defined above.

Conveniently, the vaginal assembly is unitary. Preferably, the vaginal assembly has a maximum thickness as defined above with regard to the longitudinal elements and the anterior vaginal wall element, wherein the thickness is measured disregarding any surface projections as defined below.

Preferably, the raised edge of the longitudinal elements as described above also extends around the edge of the anterior vaginal wall element.

Advantageously, the anterior vaginal wall element has a maximum width of from about 10 mm to about 60 mm, such as about 15 mm to about 50 mm, preferably from about 20 mm to about 40 mm. Wherein the width is defined as the length from one edge of the anterior vaginal wall element to the other edge. In other words, the width of the anterior vaginal wall element is substantially orthogonal to the thickness vector.

Advantageously, the proximal ends of the longitudinal elements comprise a surface profile, on their outer surface, that is adapted to be grasped by the user. Conveniently, the surface profile is in the form of raised ridges or bumps, such as hemispherical bumps. More preferably, the surface profile is in the form of concentric circular ridges adapted to be grasped with one or more fingers.

Conveniently, one or more of the proximal ends of the longitudinal elements comprises one or more projections and/or one or more slits configured for holding and/or securing suturing materials.

Conveniently, at least part of the surface of the vaginal assembly may be coated by a different material than the material of the vaginal assembly. In one example, the vaginal assembly is mainly fabricated from one material with elastic and/or resilient properties which is then at least partly coated in a second material for softness, smoothness, insulation or to make the assembly easier to handle or less traumatic for the patient. The coating may provide a smoother surface or reduced friction which also improves comfort and reduces trauma for the subject. At least part of the surface of the vaginal assembly may also be coated with a fluid or gel before or after packaging and before insertion into the vagina. This may be for lubricating and/or anesthetic purposes such that the speculum causes less discomfort during insertion and use.

In an embodiment, the vaginal speculum may have a first configuration for holding the vaginal walls of a subject apart whilst in use and a second configuration for insertion into the vagina of the subject. Preferably, the distance between the longitudinal element at their proximal end is smaller in second configuration compared to the distance in the first configuration. Advantageously, the vaginal speculum may be resiliently compressible out of the first configuration into the second configuration and resiliently expandable to return toward the first configuration. Preferably, the vaginal speculum is inserted being in the second configuration. Conveniently, whilst returning toward the first configuration the vaginal walls of the subject are being pushed apart. Advantageously, the first configuration of the vaginal speculum is configured for holding the vaginal walls of the subject apart whilst in use. Advantageously, the vaginal speculum is configured for holding the walls apart without the use of a locking engagement or locking mechanism. Preferably, the vaginal speculum does not comprise a locking mechanism. Advantageously, the vaginal speculum may be self-retaining.

The vaginal speculum may be reusable by cleaning and sterilizing the speculum after use. Preferably the presently disclosed vaginal speculum is disposable and/or for single use. Furthermore, the speculum is preferably sterilized and in a sealed package prior to use. Disposable or single-use vaginal specula eliminate the need for the costly and time consuming re-sterilization processes. Each individually packed disposable vaginal speculum as detailed above provides sterility to prevent cross-infection during gynecological procedures that may be caused by an insufficiently cleaned and sterilized re-usable speculum.

According to another aspect of the invention, there is provided an array of vaginal specula comprising a plurality of specula as defined above, wherein each speculum in the set differs in at least one dimension to each other speculum so as to provide a range of sizes of specula to fit different subject anatomies.

According to a further aspect of the invention, there is provided a sterile, hermetically sealed container, comprising a vaginal speculum as defined above, or an array of vaginal specula as defined above, for single use According to another aspect of the invention, there is provided a method for inserting a vaginal speculum into the vagina of a subject, wherein the method comprises the steps of providing a vaginal speculum as defined above and inserting the distal end of the speculum into the vagina of the subject.

Preferably, prior to insertion the longitudinal elements are transversely compressed towards each other from a first configuration, being a resting state, to a second configuration, being a compressed state. That is to say, since the longitudinal elements are connected at their distal end, it is predominantly the proximal ends of the longitudinal elements which are compressed together.

Advantageously, after insertion the longitudinal elements are released and return from the second configuration compressed state to the first configuration resting state.

The vaginal speculum being in the first configuration may be resiliently compressed into the second configuration by hand or using a tool.

Conveniently, prior to insertion the vaginal speculum, at least partially, may be coated with a fluid or a gel.

On being advanced to the desired depth within the vagina, the separating elements and vaginal wall element may be released so as to revert back from the compressed state towards their original non-compressed state. In doing so, the separating elements hold the lateral walls of the vagina apart and the anterior vaginal wall element supports and exerts pressure on the anterior wall of the vagina. As well as providing a supporting function, the anterior vaginal wall element may also act so as to rest behind the pubic bone of the subject when in the vagina and thus act as an anchor to retain the speculum in place when in use.

According to a further aspect of the invention, there is provided a method of use of the vaginal speculum as defined above during vaginal suturing after the subject has given birth.

According to another aspect of the invention, there is provided a method of providing an unobstructed view of at least the posterior part of the vaginal wall and perineum and anus during examination of a subject after said subject has given birth comprising the step of:
  inserting a vaginal speculum as defined above into the vagina of a subject using the method as defined above.

According to a further aspect of the invention, there is provided a method of suturing vaginal tissue comprising the steps of:
  inserting a vaginal speculum as defined above into the vagina of a subject using the method as defined above; and
  suturing a tear in the vagina, perineum and anal tissue of the subject.

Manufacturing techniques that may be used for the vaginal speculum include injection moulding and additive manufacturing.

Advantageously, injection moulding offers the possibility to mass-produce the disclosed vaginal specula economically.

DETAILED DESCRIPTION OF THE DRAWINGS

FIG. 1 is a side view of a vaginal assembly (100) according to the present invention. The vaginal assembly comprises two longitudinal elements (120, 104) concavely connected at their distal end arriving at a curved distal point (106). The assembly also comprises an anterior vaginal wall element (108) connected at the distal point (106) and extending in predominantly the same proximal direction as the longitudinal elements.

As can be seen, the proximal end of the anterior vaginal wall element comprises a depressed region with raised ridges, which allow the user to easily grab the anterior wall element. The proximal ends of the outer surfaces of the longitudinal elements also comprise a raised surface profile in the form of raised concentric ridges to allow the user to easily grasp these regions of the assembly.

Figure 2:
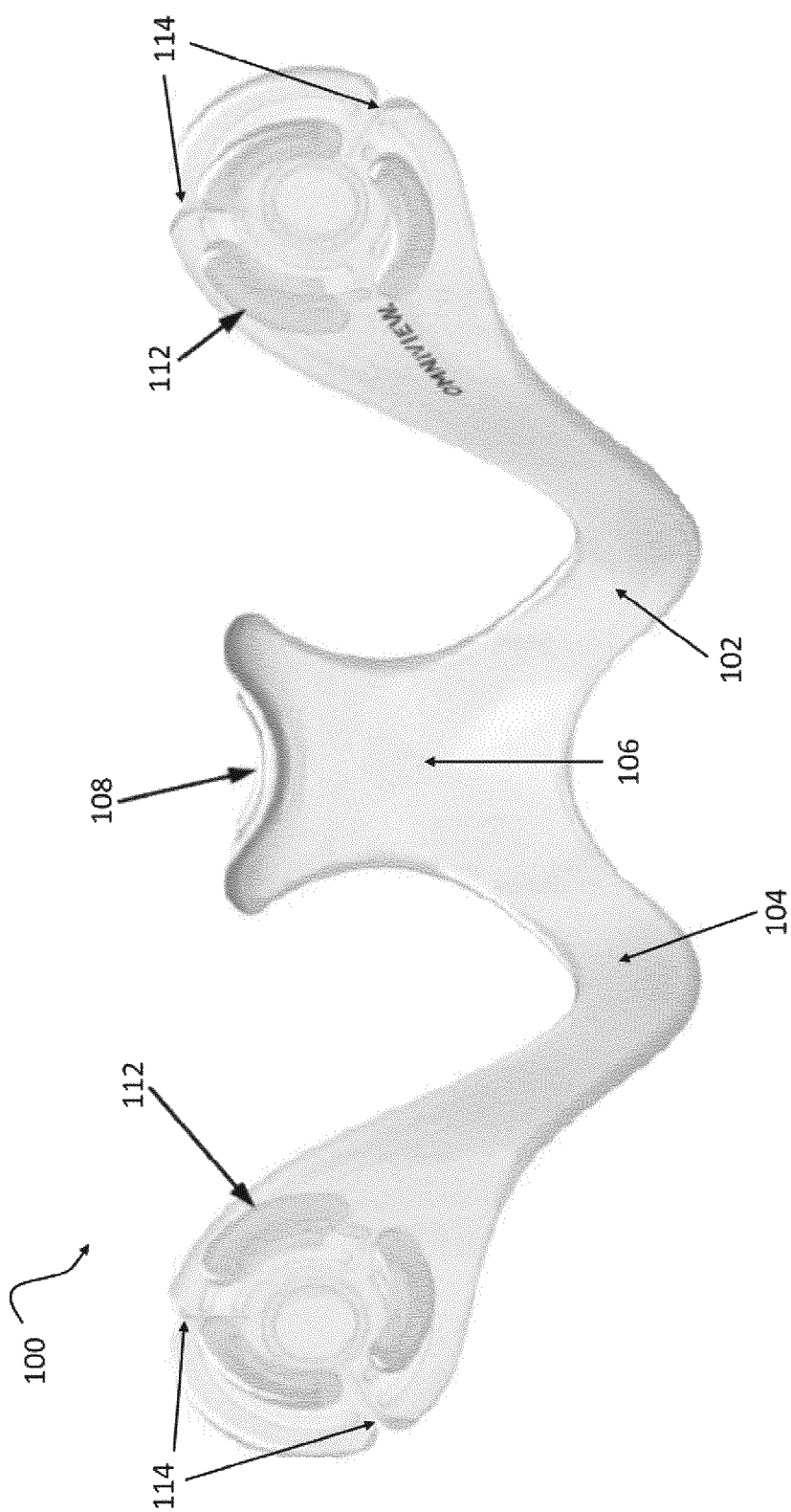
FIG. 2 is a front view of the vaginal assembly shown in FIG. 1.

The inside surfaces of the longitudinal elements also comprise projections (112) for securing suturing materials, with the slits (114) depicted in FIG. 2.

Figure 3:
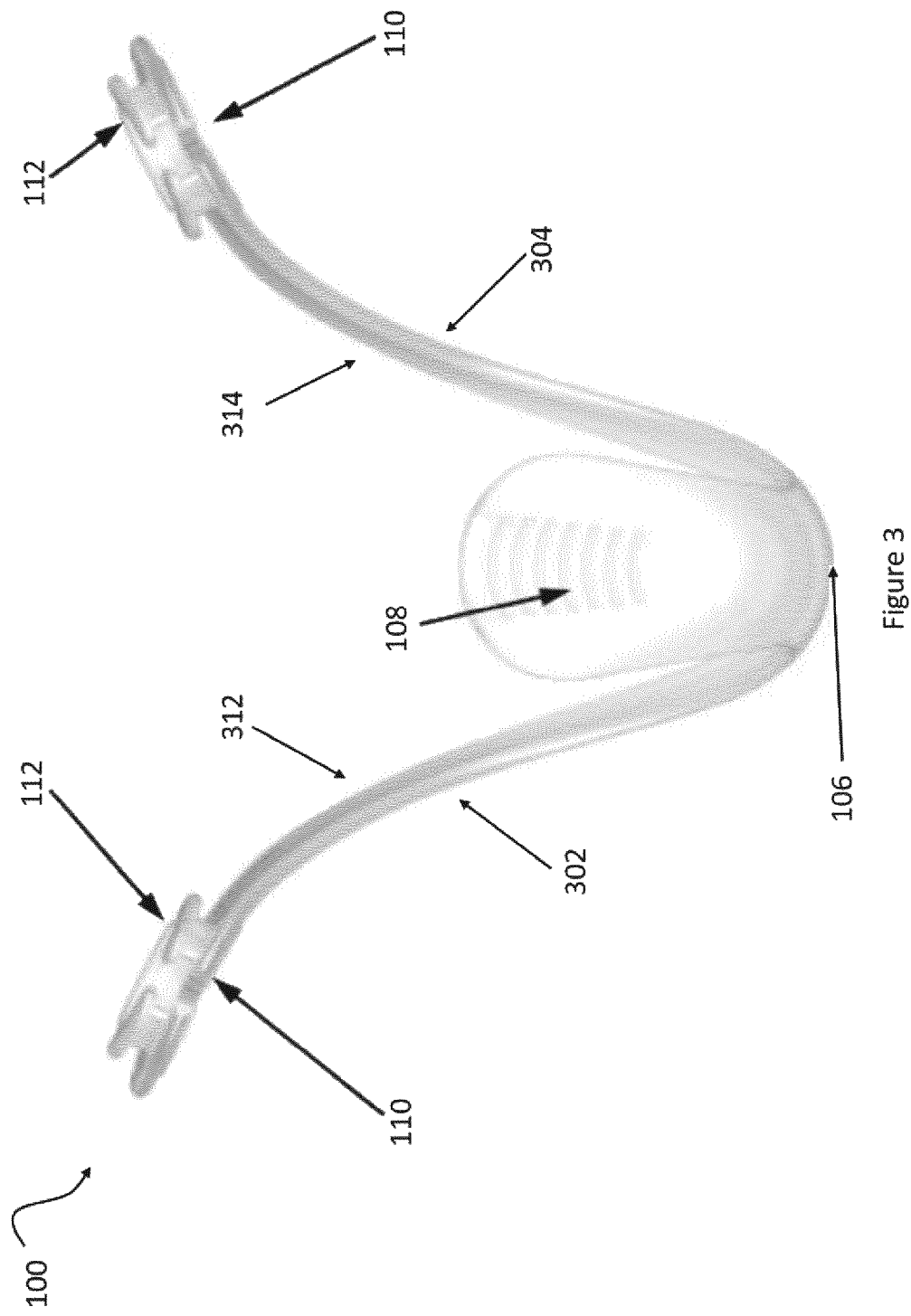
FIG. 3 is a top view of the vaginal assembly shown in FIGS. 1 and 2.

The arrow depicted with numeral (108) is pointing towards the region of the anterior wall element that is herein described as the outer surface. That is, the surface that is closest to and/or in contact with the anterior vaginal wall when in use. FIG. 3 depicts the clearest view of the outer and inner surfaces of the longitudinal elements.

FIGS. 2 and 3 are different view of the assembly depicted in FIG. 1. The annotations in FIG. 3 differ from FIG. 1 in that the outer surfaces of the longitudinal elements have been annotated with numerals 302 and 304, whereas the inner surfaces have been depicted with numerals 312 and 314.

Figure 4:
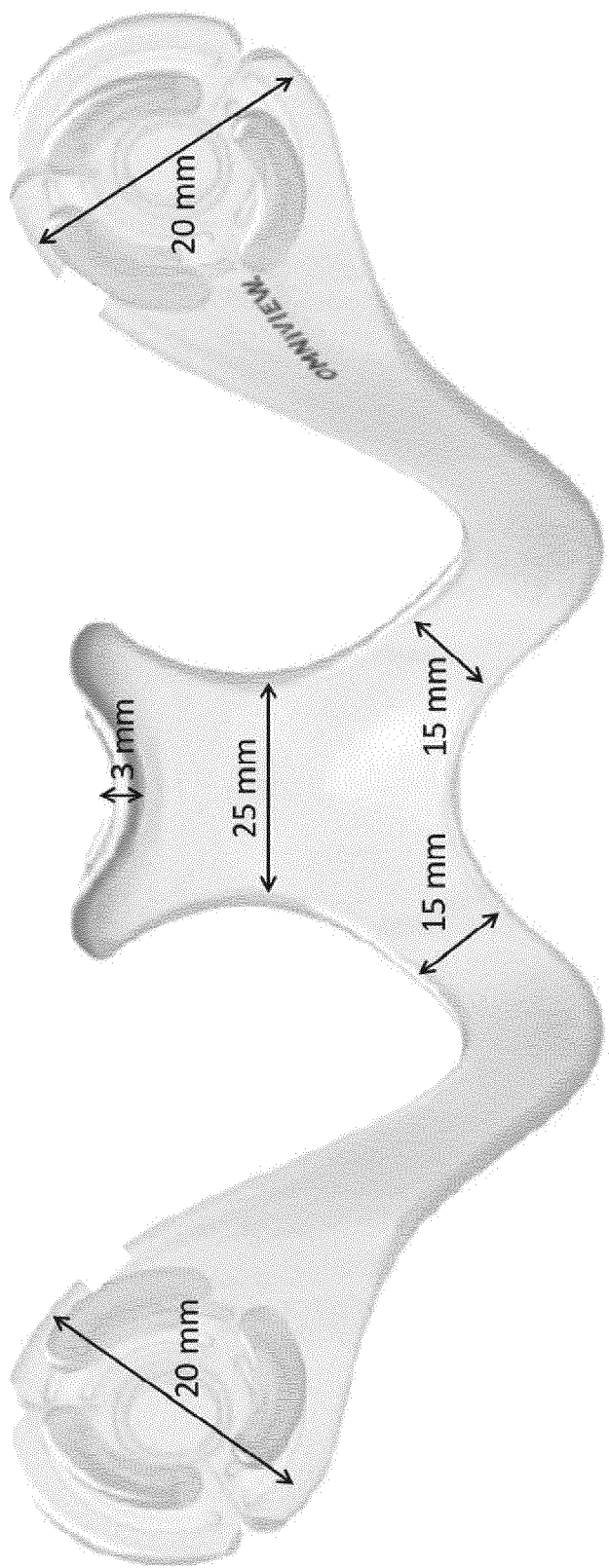
FIG. 4 corresponds to FIG. 2 and has been annotated to show the dimensions of this device.

FIGS. 4 and 5 correspond to FIGS. 2 and 3 respectively and have been annotated to detail the dimensions of the specula depicted in these figures. This speculum has a vaginal assembly where the thickness of all parts of the assembly, including the longitudinal and anterior vaginal wall elements, is approximately 3 mm.

The longitudinal elements have a width that varies from 15 mm at its narrowest section to 20 mm at its widest section and the anterior vaginal wall element has a width that varies from 25 mm at its narrowest section close to the distal end, to 37 mm at its widest point close to the proximal end.

EXAMPLES

Various specula according to specula as depicted in FIGS. 1 to 5 were prepared via injection moulding using different materials in order to assess their ability to remain in place in the vagina when in use.

Nylon 6 (Polyamide 6/PA6)

The vaginal assembly made out of polyamide 6 was found to dilate the vagina too much when in place, so the tear could not be closed resulting in discomfort for the patient. Nylon 6 has the following characteristics:

| Parameter | Value | Test Method |
| --- | --- | --- |
| Flexural Modulus | 2780 MPa | ASTM D-790 |
| Tensile Modulus | 2930 MPa | ASTM D-638 |
| Flexural Strength | 93.8 MPa | ASTM D-790 |
| Tensile Elongation | 38.8% | ASTM D-638 |

Polyoxymethylene (POM)

The vaginal assembly made out of polyoxymethylene was too smooth and did not stay in place when inserted into the vagina. POM has the following characteristics:

| Parameter | Value | Test Method |
| --- | --- | --- |
| Flexural Modulus | 3100 MPa | ASTM D-790 |
| Tensile Modulus | 3100 MPa | ASTM D-638 |
| Flexural Strength | 89 MPa | ASTM D-790 |
| Tensile Elongation | 30% | ASTM D-638 |

General Purpose Polystyrene (GPPS)

The vaginal assembly made out of GPPS was too smooth and did not stay in place when inserted into the vagina. This material also has glassy characteristics and is prone to breaking. GPPS has the following characteristics:

| Parameter | Value | Test Method |
|---|---|---|
| Flexural Modulus | 2900-3480 MPa | ASTM D-790 |
| Tensile Modulus | 3100-3170 MPa | ASTM D-638 |
| Flexural Strength | 62-100 MPa | ASTM D-790 |
| Tensile Elongation | 2-3% | ASTM D-638 |

High Impact Polystyrene

The vaginal assembly constructed of high impact polystyrene was found to have the appropriate physical characteristics to remain in place in the vagina without the aid of external retention mechanisms and, simultaneously, allow the practitioner to suture tears in the posterior vaginal wall without the assembly causing pain or discomfort to the subject and not interfering with suturing procedures. High impact polystyrene has the following characteristics:

| Parameter | Value | Test Method |
|---|---|---|
| Flexural Modulus | 2200 MPa | ASTM D-790 |
| Tensile Modulus | 2070 MPa | ASTM D-638 |
| Flexural Strength | 48 MPa | ASTM D-790 |
| Tensile Elongation | 50% | ASTM D-638 |

The retention of the speculum made out of high impact polystyrene was found to improve when the outer surfaces of the longitudinal elements and the anterior vaginal wall element that are configured to contact the vaginal walls in use were molded to have a roughness of VDI 3400-CH 45 according to the Charmilles scale of roughness as measured according to ISO 1302 (class N10), Such a surface has the following characteristics:

| | |
|---|---|
| Ra | 18 μm |
| Rt max. | 144 μm |
| approx. 8 * Ra | |

Wherein no. CH=20 log(10Ra) (micro mm)

The invention claimed is:

1. A vaginal speculum comprising:
a vaginal assembly comprising two longitudinal elements each having a proximal and distal end and being connected towards their distal ends, wherein each longitudinal element comprises an inner and an outer surface;
wherein the vaginal speculum is configured for holding the vaginal walls of the subject apart via the longitudinal elements, wherein the outer surfaces of the longitudinal elements are configured to be in contact with the vaginal walls of the subject whilst in use and the vaginal assembly is fabricated at least partially from an elastic material having a flexural modulus of from about 1000 MPa to about 3500 MPa, and wherein one or both of the outer surfaces of the longitudinal elements that are configured to be in contact with the vaginal walls of the subject whilst in use have a surface roughness of from about 5 to 31 micrometers Ra.

2. The vaginal speculum according to claim 1, wherein the vaginal speculum is fabricated entirely from an elastic material.

3. The vaginal speculum according to claim 1, wherein the elastic material has a flexural modulus of from about 1500 MPa to about 3000 MPa.

4. The vaginal speculum according to claim 1, wherein the elastic material has a tensile modulus of from about 1000 MPa to about 3000 MPa.

5. The vaginal speculum according to claim 1, wherein the elastic material has a tensile modulus of from about 1900 MPa to about 2500 MPa.

6. The vaginal speculum according to claim 1, wherein the elastic material has a flexural strength of from about 10 MPa to about 100 MPa.

7. The vaginal speculum according to claim 1, wherein the elastic material has a tensile strength of from about 5 MPa to about 40 MPa.

8. The vaginal speculum according to claim 1, wherein the vaginal speculum is fabricated from a polymeric material.

9. The vaginal speculum according to claim 8, wherein the polymeric material is selected from the group consisting of nylon, silicone, polyethylene (PE), polyethylene (PE), polypropylene (PP), polystyrene (PS), high impact polystyrene (HIPS), polyvinyl chloride (PVC), polyester, polycarbonate, polysulfone, poly-p-xylylene, and mixtures thereof.

10. The vaginal speculum according to claim 1, wherein the vaginal assembly further comprises an anterior vaginal wall element configured for supporting the anterior vaginal wall.

11. The vaginal speculum according to claim 10, wherein the anterior vaginal wall element is connected at a distal end of the vaginal assembly, extending in the proximal direction from the distal end.

12. The vaginal speculum according to claim 10, wherein the anterior vaginal element is in the shape of a tongue.

13. The vaginal speculum according to claim 10, wherein the vaginal assembly is configured for supporting the anterior vaginal wall after insertion into the vagina.

14. The vaginal speculum according to claim 1, wherein at least 50% of one, or both, of the outer surfaces of the longitudinal elements configured to be in contact with the vaginal walls of the subject whilst in use has a roughness from about 5 to 31 micrometers Ra.

15. The vaginal speculum according to claim 14, wherein the area of roughness is continuous or discontinuous.

16. An array of vaginal specula comprising a plurality of specula according to claim 1, wherein each speculum in the plurality differs in at least one dimension to each other speculum so as to provide a range of sizes of specula to fit different subject anatomies.

17. A sterile, hermetically sealed container, comprising a vaginal speculum according to claim 1, or an array of the vaginal specula, wherein each vaginal speculum in the set differs in at least one dimension to each other so as to provide a range of sizes of specula to fit different subject anatomies, for single use.

18. A method of providing an unobstructed view of at least the posterior part of the vaginal wall during examination of a subject after said subject has given birth comprising the step of: inserting the distal end of a vaginal speculum as claimed in claim 1 into the vagina of a subject.

19. A method of suturing vaginal tissue comprising the steps of:
inserting the distal end of a vaginal speculum according to claim 1 into the vagina of a subject; and
suturing a tear in the vaginal tissue of the subject.

* * * * *